United States Patent [19]
Watanabe et al.

[11] 3,958,014
[45] May 18, 1976

[54] PROCESS FOR PREPARING INJECTION-PURPOSE FLUOROCARBON EMULSION CAPABLE OF CARRYING OXYGEN

[75] Inventors: Ryozo Watanabe, Takatsuki; Tadakazu Suyama, Hirakata; Kazumasa Yokoyama, Suita; Yohei Odaka, Kyoto, all of Japan

[73] Assignees: The Green Cross Corporation, Osaka; Tanabe Seiyaku Co., Ltd., both of Japan

[22] Filed: Mar. 20, 1973

[21] Appl. No.: 343,148

[30] Foreign Application Priority Data
Sept. 5, 1970   Japan.......................... 78023/70
July 29, 1971   Japan.......................... 57003/71

Related U.S. Application Data

[63] Continuation-in-part of Ser. No. 177,434, Sept. 2, 1971, abandoned.

[52] U.S. Cl. ............................................. 424/366
[51] Int. Cl.² ........................................ A61K 45/00
[58] Field of Search ................................... 424/366

[56] References Cited
OTHER PUBLICATIONS
Science Vol. 152, 1755–1756 (1966).
Symposium on Inert Liquids for Biological Oxygen Transport–Atlantic City, N.J., Apr. 13, 1969 – Fed. Pro. 1970, pp. 1695–1697, 1758–1763.

*Primary Examiner*—Frederick E. Waddell
*Attorney, Agent, or Firm*—Cushman, Darby & Cushman

[57] ABSTRACT

An injectable fluorocarbon emulsion capable of carrying oxygen, which can be used as artificial blood and organ perfusate, is prepared by emulsifying a fluorocarbon, having an ability to dissolve at least 30 V/V % of oxygen under a 100% oxygen atmosphere at an atmospheric pressure, in an aqueous salt solution with a surfactant, centrifuging the resulting aqueous emulsion thereby to reduce the fluorocarbon particles in the emulsion in size to particle sizes of the order of about 0.05 to 0.25 $\mu$, and then sterilizing the thus obtained emulsion under rotation. The resulting fluorocarbon emulsion can be used as an emergency blood substitute for transfusion.

3 Claims, No Drawings

PROCESS FOR PREPARING INJECTION-PURPOSE FLUOROCARBON EMULSION CAPABLE OF CARRYING OXYGEN

CROSS REFERENCE TO RELATED APPLICATION

This application is a continuation-in-part application of our earlier copending application Ser. No. 177,434, filed Sept. 2, 1971, now abandoned.

BACKGROUND OF THE INVENTION

This invention relates to a process for preparing an injectable fluorocarbon emulsion capable of carrying oxygen which may be administered to mammals suffering from severe blood loss.

Prior procedures in the treatment of blood loss of patients in which the blood volume has been reduced by no more than 1500 ml include administration of an injectable liquid, having a colloidal osmotic pressure, for example, dextran, or an electrolyte solution such as Lactate Ringer's solution, thereby to prevent shock caused from the bleeding. These materials are known generally as plasma expanders. However, in the event that the bleeding exceeds 1500 ml in volume, the amount of oxygen carried by red blood-cells in the remaining blood becomes rapidly depleted, and tissue respiration, at least at the peripheral tissues, becomes insufficient. Therefore, loss exceeds about 1500 ml volume expanders, such as dextran or electrolyte solutions are ineffective and a blood transfusion is required.

Preparations having an ability to carrying oxygen in laboratory animals have been studied by a number of investigators, but not until recently has it been known that such preparations could have a potential life saving effect when injected into such animals. In 1966, L. C. Clark Jr. as described in Science, 152 1755 (1966) succeeded in keeping mice living for a relatively long period of time by immersing the mice in certain types of fluorocarbon solutions, and studies on utilization of fluorocarbons as an oxygen carrier in living bodies were started at that time. In 1968, R. P. Geyer reported that total blood of a mouse was exchanged with a fluorocarbon emulsion by blood transfusion and the mouse could be kept living for a few hours, this work is described in "Organ Perfusion and Preservation", Appleton-Centry Crafts, page 85 (1968). Later Clark et al. reported in Chemical and Engineering News, Dec. 15 (1969), page 51 that total blood volume of a dog was exchanged with a fluorocarbon emulsion by blood exchange transfusion, and the dog could be successfully kept living for a relatively long time.

We have now made studies and found a process for preparing an injectable preparation having the ability to carry oxygen, and have found a novel process for preparing, on a mass-production scale, an injectable oxygen-carrying emulsion capable of keeping mammals such as dogs and monkeys living for a long period of time by blood exchange transfusion.

Accordingly it is an object of the present invention to provide a process for preparing an injectable emulsion having the ability to carry a significant amount of oxygen.

Another object of the present invention is to provide a process for preparing, on a mass-production scale, an injectable emulsion capable of keeping mammals such as dogs and monkeys living for a long time by blood exchange transfusion.

Another object of the present invention is to provide a process for preparing a fluorocarbon emulsion applicable as an "artificial blood" and organ perfusate.

Other objects and advantages of the present invention will be apparent from the following description.

DETAILED DESCRIPTION OF THE INVENTION

According to the present invention a process is provided and described herein for preparing an injectable fluorocarbon emulsion having the ability to carry oxygen, which process is characterized by emulsifying in an aqueous salt solution a specific type of a fluorocarbon having the ability to dissolve at least 30 V/V % oxygen in the fluorocarbon under an 100% oxygen atmosphere under the ambient atmospheric pressure with yolk lecithin as an emulsification agent, centrifuging the resulting aqueous emulsion thereby to divide and disperse fluorocarbon particles within the emulsion to particle sizes ranging from 0.05 to 0.25, and then sterilizing the thus-formed emulsion while rotating.

As used herein the term physiologically acceptable electrolyte solution includes those solutions of an electrolyte or electrolytes adapted for injection. Illustrative are lactated potassic saline injection, Ringer's injection, lactated Ringer's injection, Ringer's solution, lactated Ringer's solution, sodium acetate, sodium chloride and sodium lactate injection. These and other preparations are described in Remington's Pharmaceutical Science, 13th Edition, pages 914 –922 (1965) under the heading "electrolytes". Other plasma expanders are described in Goodman and Gillman, The Pharmacological Basis of Therapeutics, 3rd Edition, pages 754–794 (1965). The disclosures of both of the above are hereby incorporated by reference. We prefer to use lactated Ringer's solution and it is with reference thereto that the following description is cast.

The present invention is specific in a number of aspects both as to the nature of materials used and the particle sizes and the like, of the resulting emulsion. These parameters were not arrived at casually but rather were determined through a systematic course of investigations which are discussed below. Parameters not expressly discussed below will be apparent to the skilled worker and appropriate conditions will be appreciated. Fluorocarbon - The sole fluorocarbons applicable to the present invention are perfluorodecalin or perfluoromethyldecalin or their mixture. A surfactant or emulsifying agent is also used and surfactant capable of emulsifying and stabilizing these fluorocarbons is egg yolk lecithin and preferably in an amount of from about 3 W/V % to 5 W/V % based on emulsion. There are a number of good reasons for the specificity of the fluorocarbon compounds that are useful. For example when an emulsion of FC-43 (perfluorotributylamine) and Freon $E_4$ (2-monohydro-nonacosafluoro3,6,9,12-tetraoxa-5,8,11-trimethylpentadecane) is injected into veins of laboratory animals most of these fluorocarbons are accumulated in the animal's liver and spleen, up to 40% of the fluorocarbon administered remains in the organs after 8 weeks from administration, and the toxicity resulting from the accumulation appears. Similarly when an emulsion of FX-80 (perfluorobutyltetrahydrofuran) is injected into the veins of a laboratory animal, a remarkable lung hazard appears, and its toxicity is quite high.

On the other hand when an emulsion of perfluorodecalin and perfluoromethyldecalin is injected into the veins, of laboratory animals their accumulated in the animal's liver and spleen is very small. For example, perfluorodecalin is as low as zero % and perfluoromethyldecalin is 1.5% even after 8 weeks.

Thus the fluorocarbons of the present invention are quite properly limited to perfluorodecalin, perfluoromethyldecalin and their mixture for the foregoing reasons. Applicants have found that with these particular fluorocarbon materials the surfactant of choice is egg yolk lecithin. Other surfactants produce less stable emulsions hence are less desirable, as described below.

Emulsifier — When the fluorocarbon selected is perfluorodecalin and perfluoromethyldecalin but the surfactant is polyoxyethylene-polyoxypropylene (Pluronic F68) we have found that yolk lecithin is preferable, because the emulsion prepared by lecithin is more stable, as shown in Table 1. The table shows the change in mean particle size measured in microns observed at two different times, the first just after preparation and the second one after standing for 48 hours. Pluronic F68 is good for emulsifying FC-43 or Freon $E_4$, however as previously explained these fluorocarbons are not preferred.

Table 1

| Emulsion | Stability of Various Emulsions Mean particle size ($\mu$) | |
|---|---|---|
| (fluorocarbon content: 25 W/V % | Just after emulsification | After 48 hrs. |
| Perfluorodecalin-Pluronic F68 | 0.12 | 1 or more |
| Perflurodecalin-yolk lecithin | 0.14 | 0.14 |
| Perfluoromethyldecalin-Pluronic F68 | 0.11 | 1 or more |
| Perfluoromethyldecalin-yolk lecithin | 0.12 | 0.12 |
| Reference | | |
| FC-43-Pluronic F68 | 0.08 | 0.08 |
| FC-43-Yolk lecithin | 0.12 | 0.12 |
| Freon $E_4$-Pluronic F68 | 0.14 | 0.14 |
| Freon $E_4$-Yolk lecithin | 0.14 | 0.14 |

The optimal concentration of yolk lecithin as an emulsifier was obtained from a series of investigations as shown in Table 2. We have observed that the stability of the emulsions prepared with less than 3 W/V % of yolk lecithin are lowered, and toxicity of an emulsion prepared with more than 5 W/V % of it was increased. Accordingly the amount of yolk lecithin is of the order of about 3 W/V % to about 5 W/V %.

Table 2

Stability and toxicity of perfluoromethyldecalin emulsion prepared with various concentration of yolk lecithin

| Emulsion concentration of (W/V %) | | Tests | Mean particle size | | mice-LD$_{50}$ (g/kg b.w.) | |
|---|---|---|---|---|---|---|
| Perfluoromethyldecalin | Yolk lecithin | | Just after emulsification | After 2 weeks | Just after emulsification | After 2 weeks |
| 25 | 2 | | 0.27 $\mu$ | more than 0.5 $\mu$ | 15.2 | 3.4 |
| 25 | 3 | | 0.14 $\mu$ | 0.14 $\mu$ | 29.4 | 29.1 |
| 25 | 4 | | 0.12 $\mu$ | 0.12 $\mu$ | 30.1 | 30.3 |
| 25 | 5 | | 0.11 $\mu$ | 0.12 $\mu$ | 30.1 | 29.8 |

Table 2-continued

Stability and toxicity of perfluoromethyldecalin emulsion prepared with various concentration of yolk lecithin

| Emulsion concentration of (W/V %) | | Tests | Mean particle size | | mice-LD$_{50}$ (g/kg b.w.) | |
|---|---|---|---|---|---|---|
| Perfluoromethyldecalin | Yolk lecithin | | Just after emulsification | After 2 weeks | Just after emulsification | After 2 weeks |
| 25 | 6 | | 0.11 $\mu$ | 0.11 $\mu$ | 27.6 | 28.4 |

Particle size — Another important feature of the present invention is the particle size of the emulsion. We have found that the particle sizes of the emulsion should range from about 0.05 to 0.25 microns because within this range the particle sizes provide the best results as described below.

The reaction of the test animal to particle sizes of an emulsion injected into it is not explained merely by the size of the capillary vessel or its shrinkage phenomenon, but it also depends upon the nature of the components in the emulsion. Take, for instance, a fat emulsion and a fluorocarbon emulsion. It is reported in the literature that the particle sizes of fat emulsion for chemical injection most commonly used in Europe and Japan is between 0.1 and 1 microns according to Geyer R. P. et al; The J. of the Am. Oil Chemists' Society, Vol. 32, 365-370, 1955; Schuberth, O. and Wretlind, A; Acta Chirugica Scan., Suuplement 278, 3–21, 1961. It is also reported in the literature that the particle sizes of chylomicron, fat absorbents present in the blood vessels of living mammal, amount to 1 micron. Therefore it can be said that the presence of a fat emulsion having as the largest particle size up to 1 micron has no unfavorable influence upon the living body at all. On the other hand, in the case of fluorocarbon emulsion, we have determined that from the death of animals the presence of fluorocarbon particles of more than 0.375 microns in size in the blood vessels is apparently hazardous to animals. In other words when a fluorocarbon emulsion having particle sizes of no greater than 0.375 microns was injected into mice all of the mice were living after a period of 72 hours, whereas when an equivalent amount of a fluorocarbon emulsion having a particle size as large as 1.0 micron was injected into mice, all ten mice were killed after 72 hours. The results of our investigation are shown in Table 3 and the particle size distributions in these experiments are shown in Table 4. We have clarified the tolerable particle size range for injectable fluorocarbon emulsions through precise measurement of particle sizes of the fluorocarbon emulsion and a detailed study on the relationship between the death rate and particle sizes. In measuring the particle sizes a centrifugal precipitation method was used based on the Stokes and Bostok principles, and the particle sizes thus measured were confirmed and found to be in accordance with those measured by a sophisticated electron microscope. Based on the above it will be apparent then, that the particle size range of the emulsion injected will vary depending on the nature of the material injected; for fluorocarbons the tolerable range is much smaller than for fats.

Table 3

| Sample (particle size distributon) | Particle size distribution and ratio of the dead mice Number of dead mice per number of tested mice |
|---|---|
| Emulsion obtained by ultrasonic treatment (0.05 – 1.0 μ) | 10/10 |
| Emulsion obtained by injection emulsification (0.05 – 0.75 μ) | 8/10 |
| Supernatant emulsion obtained by centrifuge (0.05 – 0.25 μ) | 0/10 |
| Emulsion obtained by rotary sterilization (0.05 – 0.375 μ) | 0/10 |

In this test, each sample was prepared by mixing 25 W/V % perfluoromethyldecalin and 4 W/V % of yolk lecithin with a lactate Ringer's solution. The dose of perfluoromethyldecalin in mice was 15 g/kg body weight, by intravenous injection, and the condition of the mice was observed after 72 hours.

Table 4

| Sample | Particle size (μ) | The particles size distribution | | | | |
|---|---|---|---|---|---|---|
| | | 0.05 to 0.25 | 0.25 to 0.375 | 0.375 to 0.5 | 0.5 to 0.75 | 0.75 to 1.0 |
| Emulsion obtained by ultrasonic treatment | | 73% | 18% | 6% | 2% | 1% |
| Emulsion obtained by injection emulsification | | 72% | 21% | 6% | 1% | 0% |
| Supernatant emulsion obtained by centrifuge | | 100% | 0% | 0% | 0% | 0% |
| Emulsion obtained by rotary sterilization | | 87% | 13% | 0% | 0% | 0% |

The particle size distribution was measured by a centrifugal precipitation method.

Furthermore, we have found that the particle size of the fluorocarbon emulsion has an influence upon the persistence of the fluorocarbon in the blood vessels. For instance about 70% of the fluorocarbon administered to a test animal could be found in blood stream after 6 hours from the veinous injection of an emulsion having particle sizes of 0.375 microns or less, whereas about 50% of the fluorocarbon administered could be found in the blood stream when an emulsion having particle sizes of 1 micron or less was injected in vein. Accordingly one concludes that the fluorocarbon having a larger particle size rapidly disappears from the blood stream, and the choice of particle sizes has an important significance upon the ability of the fluorocarbon to act as an oxygen carrier.

As explained above, it is essential that the fluorocarbon emulsion according to the present invention contains no particle sizes of more than 0.375 microns, and a combination of steps for producing such emulsion having the above particle size also has an important significance. We have found that the process of emulsifying the fluorocarbon and surfactant is most expeditiously carried out in a Manton-Gaulin homogenizer, although other types of equipment may be used, while centrifuging and sterilizing are done under rotation. This particular combination of steps is important for producing the desired fluorocarbon emulsion.

The concentration of fluorocarbon or fluorocarbons in the emulsion is arrived at according to the following calculation. The stability and oxygen transport ability are influenced by the fluorocarbon concentration and as shown above, the emulsion which contained less than 30 W/V % of fluorocarbon is most stable, while on the other hand the emulsion which contained more than 50 W/V % is extremely unstable. Of course, the oxygen transport ability is controlled by the concentration of fluorocarbon in the emulsion and the higher the concentration the higher the oxygen transport ability. All factors being considered, however, we prefer an amount of fluorocarbon of about 10 to 30 W/V % and more preferably from 25–30 W/V % of fluorocarbon or fluorocarbons.

Emulsion Preparation — Emulsification according to the present invention is carried out in the following manner: First, a predetermined amount of the egg lecithin is suspended in a suitable aqueous electrolyte solution, such as Lactate Ringer's solution and a fluorocarbon is added thereto. Of course other physiologically acceptable electrolyte solutions of the type presently used as blood volume replacements, such as normal saline solution, may also be used. The resulting mixture is stirred in a homo-blender or by a propeller stirrer to prepare a crude emulsion. The crude emulsion is further emulsified and the particles broken down in a Manton-Gaulin type injection emulsifier. The specific emulsifying conditions are such that, while the crude emulsion is kept at 50°C or less, the crude emulsion is injected under a pressure of 140 kg/cm$^2$ at the first stage, under a pressure of 500 kg/cm$^2$ at the second and third stages, under a pressure of 500 kg/cm$^2$ at the second and third stages, under a pressure of 560 kg/cm$^2$ at the fourth stage and under a pressure of 140 kg/cm$^2$ at the fifth stage. Generally the temperature of the emulsification step is maintained below about 50°C and preferably between about 30° and 50°C. Fluorocarbon particles of the thus obtained emulsion are distributed in a particle size range of about 0.05 μ to 1.0 μ, when observed by an electron microscope.

We have found that a centrifugal separation step is useful for finely dividing the fluorocarbon particles, and it is the first requirement for the present invention to adjust the particle size distribution to a narrower range by the centrifugal operation for the reasons explained above. A De Laval or Saval type centrifuge is suitable for the centrifugal operation although other equipment may be acceptable, and it is advantageous in a mass production scale to continuously carry out the centrifugal separation by such a centrifuge. In the case of the De Laval type centrifuge, a type BP15 K is used and the emulsion is passed through the centrifuge at a flow rate of 30 l/hr and a supernatant liquid is collected, while setting the motor and the rotor at 1500 rpm and 9000 rpm, respectively. In the case of the Saval type centrifuge the emulsion is passed through at a flow rate of 6 l/hr, while setting the centrifuge at 1000 × g. The particle sizes of the fluorocarbon after the centrifugal separation are in a range from 0.05 μ to 0.25 μ, and the animal test results reveal that the thus prepared emulsion can be satisfactorily used, as shown in Table 3 and discussed above.

Sterilization — To use the thus prepared emulsion as an injection material safely it is necessary to first sterilize the emulsion. However, when the emulsion is heated, particles of the emulsion usually start to join together a coalescence and are aggregated, and consequently the emulsion undergoes phase separation. We have found that to sterilize the emulsion of the present invention without joining together and aggregating the particles, it is useful to slowly rotate the emulsion in a sterilizer. Thus another critical requirement for the present invention to sterilize the emulsion under rotation.

Sterilization times and temperatures are of course, interrelated and generally the time and temperature are chosen to assure a sterile product. Temperatures of the order of about 110° to 120°C or even higher may be used and times as long as 15 minutes may be employed all provided, of course, that rotation is maintained. For example, when the emulsion is sterilized at 115°C for 15 minutes while keeping a container for the emulsion at stationary, the emulsion undergoes complete phase separation, whereas when the emulsion undergoes rotation at 12 rpm under the same conditions as above, only slight groth of the particle sizes is observed, that is the particle sizes of 0.05 $\mu$ to 0.25 $\mu$ are increased only to a range from 0.05 $\mu$ to 0.375 $\mu$. When the emulsion is injected in an animal after this rotary sterilization step has been completed the best results can be obtained as shown in Table 3.

The particle sizes of the fluorocarbon have all been determined from electron microscope images, and one example of the particle size distribution is shown in Table 2.

The present invention will now be described in more detail with reference to the following examples. Unless otherwise indicated all parts and percentages are by weight.

EXAMPLE 1

52.6 g of sodium chloride, 3.7 g of potassium chloride, 1.4 g of magnesium chloride, 22.2 g of sodium acetate and 50.2 g of sodium gluconate were dissolved in 1000 ml of distilled water for injection to prepare an aqueous electrolyte solution, and the resulting solution was diluted to 8 l. 400 g of yolk lecithin was suspended in the solution and 3.0 kg of perfluorodecalin was added to the suspension. The mixture was vigorously stirred with a propeller stirrer for about 30 minutes to produce a crude emulsion. Distilled water was added to the crude emulsion to make total volume 10 l. The crude emulsion was placed in the liquid tank of a Manton-Gaulin injection-type emulsifier and emulsified by injecting the emulsion under a pressure of 140 kg/cm$^2$ at the first stage, under a pressure of 500 kg/cm$^2$ at the second and third stages, under a pressure of 560 kg/cm$^2$ at the fourth stage and under a pressure of 140 kg/cm$^2$ at the fifth stage, while keeping the temperature between 40° to 50°C.

All of the emulsion was then passed through a De Laval type centrifuge, type BK15K (motor: 1500 rpm; rotor: 9000 rpm) at a flow rate of 30 l/hr for about 20 minutes and the supernatant emulsion was collected. However, 500 ml of the emulsion initially passed was returned to the centrifuge because of poor centrifuging effect and re-centrifuged. By the centrifugal operation, about 9.7 l of the emulsion containing 30 W/V % of fluorocarbon was obtained. The thus obtained emulsion was fractioned in injection vials, and the vials were plugged and placed in a rotary sterilizer. The emulsion was sterilized at 115°C under rotation at 12 rpm for 15 minutes. The emulsion after the rotary sterilization contained about 90% of fluorocarbon having particle sizes of 0.05 $\mu$ to 0.25 $\mu$ and about 10% of that having particle sizes of 0.25 $\mu$ to 0.375 $\mu$, but contained no fluorocarbon having larger particle sizes.

EXAMPLE 2

40 g of yolk lecithin was suspended in 800 ml of Ringer's solution containing sodium lactate. 250 g of perfluoromethyldecalin was added to the thus obtained suspended solution and the resulting mixture was stirred at room temperature in a homomixer for 15 minutes to produce a crude emulsion. More Ringer's solution containing sodium lactate was added to the crude emulsion to make the total volume 1 l. Emulsification was carried out in the same manner as in Example 1 and the emulsion was placed in a Saval type continuous centrifuge. The emulsion was centrifuged at 1000 × g by passing all the amount of the emulsion therethrough for 10 minutes, whereby about 1 l of emulsion containing about 25 W/V % of fluorocarbon was obtained. The emulsion was sterilized under rotation under the same conditions as in Example 1, whereby an emulsion having almost same particle size distribution as in Example 1 was obtained.

EXAMPLE 3

The emulsions prepared in examples 1 and 2 were used and the blood of dogs and monkeys was exchanged with these emulsions until the hematocrit value reached 3%. A total of 18 dogs and 7 monkeys were used and almost the entire blood volume was successfully exchanged with the emulsions by operational procedure based on transfusion. The animals survived normally for three months and after the three months they were sacrificed and dissected, to study potential organ abnormalities but no abnormal state was observed throughout all the tissues. From these experiments we have concluded that the fluorocarbon emulsion as described herein and whose particle sizes were adjusted to 0.05 to 0.375 had the ability to carry oxygen and carbon dioxide throughout the living body of the animals tested as a substitute for red blood-cells.

We claim:
1. A process for preparing an injectable emulsion of fluorocarbon particles adapted to carry oxygen in an aqueous vehicle, said process comprising
   a. emulsifying an aqueous physiologically acceptable electrolyte solution containing from about 10 up to at most about 30 W/V %, based on the emulsion, of a fluorocarbon selected from the group consisting of perfluorodecalin, perfluoromethyldecalin and their mixture and from about 3 W/V % to about 5 W/V %, based on the emulsion, of yolk lecithin, and continuing the emulsification until said fluorocarbon particles are dispersed in the aqueous phase and distributed in a particle range size of from about 0.05 to about 1.0 microns by injecting the emulsion with a Manton-Gaulin type injection emulsifier under a pressure of 140 kg/cm$^2$ at the first stage, under a pressure of 500 kg/cm$^2$ at the second and third stages, under a pressure of 560 kg/cm$^2$ at the fourth stage and under a pressure of 140 kg/cm$^2$ at the fifth stage at 50° C or less;
   b. continuously centrifuging the aqueous emulsion of step (a) with a De Laval type centrifuge at a flow rate of 30 l/hour while setting the mortar and the rotor at 1500 rpm and 9000 rpm, respectively, or with a Saval type centrifuge at a flow rate of 6 l hour, while setting the centrifuge at 100 × g, thereby reducing the particle size of said fluorocarbon particles into particles of the order of about 0.05 to about 0.25 microns and c. subjecting the aqueous emulsion of step (b) to sterilization at 110° to 120° C for 15 minutes while rotating said emulsion at 15 rpm, thereby preventing substantial agglomeration of said fluorocarbon particles in said emulsion while sterilizing said emulsion.

2. The process of claim 1, wherein the particle size of said fluorocarbon particles following step (c) is of the order of about 0.05 to about 0.375 microns.

3. The process of claim 1, wherein the amount of said fluorocarbon is from about 25 to about 30 W/V %.

* * * * *